United States Patent
Lewis et al.

(10) Patent No.: US 8,185,623 B2
(45) Date of Patent: May 22, 2012

(54) SELECTIVELY ROUTING PATIENT DATA BETWEEN FIELD DEVICES AND TREATMENT CENTER DESTINATIONS

(75) Inventors: Dana Lewis, Woodinville, WA (US); Randy L. Merry, Woodinville, WA (US); Richard C. Nova, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 178 days.

(21) Appl. No.: 12/394,881

(22) Filed: Feb. 27, 2009

(65) Prior Publication Data

US 2009/0222539 A1    Sep. 3, 2009

Related U.S. Application Data

(60) Provisional application No. 61/067,591, filed on Feb. 29, 2008.

(51) Int. Cl.
*G06F 15/16* (2006.01)

(52) U.S. Cl. ... 709/224; 709/202; 709/203; 340/539.12; 455/404.2; 455/414.2

(58) Field of Classification Search ........... 709/203, 709/217, 224, 238, 202; 340/539.12, 539.11; 455/404.2, 414.2

See application file for complete search history.

(56) References Cited

U.S. PATENT DOCUMENTS

| | | | |
|---|---|---|---|
| 5,339,821 A | 8/1994 | Fujimoto | |
| 5,544,661 A | 8/1996 | Davis et al. | |
| H1896 H * | 10/2000 | Hoffpauir et al. | 455/433 |
| 6,602,191 B2 | 8/2003 | Quy | |
| 6,681,003 B2 | 1/2004 | Linder et al. | |
| 6,783,492 B2 * | 8/2004 | Dominguez et al. | 600/365 |
| 6,970,737 B1 | 11/2005 | Brodnick et al. | |
| 7,076,287 B2 | 7/2006 | Rowlandson | |

(Continued)

FOREIGN PATENT DOCUMENTS

EP    1 219 235 A1    7/2002

(Continued)

OTHER PUBLICATIONS

S. Rathmore et al., "Regionalization of ST-Segment Elevation Acute Coronary Syndromes Care," Journal of the American College of Cardiology, vol. 47, No. 7, pp. 1346-1349, 2006.

(Continued)

*Primary Examiner* — David Lazaro
(74) *Attorney, Agent, or Firm* — Marger Johnson & McCollom PC

(57) ABSTRACT

Techniques for routing event data from a field device, such as an external defibrillator, to a selected subset of a plurality of possible destinations are described. The event data may include physiological data of the patient, such as a 12-lead electrocardiogram (ECG). The destinations may be associated with one of a plurality of patient treatment centers, and may include, as examples, computing device, printers, displays, personal digital assistants, or web-accessible accounts. In some examples, a server maintains user-configurable information or rules for at least some of the destinations, and uses the information or rules for determining whether event data received from a field device is routed to the destination. In some examples, the server may also make the routing determination based on an analysis of event data, such as a determination as to whether the event data indicates that the patient is suspected to be experiencing an acute myocardial infarction.

51 Claims, 9 Drawing Sheets

U.S. PATENT DOCUMENTS

| | | | |
|---|---|---|---|
| 7,138,902 | B2 | 11/2006 | Menard |
| 7,258,665 | B2 | 8/2007 | Kohls et al. |
| 7,321,862 | B2 * | 1/2008 | Rosenfeld et al. ............ 705/3 |
| 7,586,956 | B1 * | 9/2009 | Mishra et al. ............ 370/522 |
| 2002/0087355 | A1 | 7/2002 | Rowlandson |
| 2002/0107206 | A1 | 8/2002 | Coolidge et al. |
| 2002/0196141 | A1 * | 12/2002 | Boone et al. ............ 340/540 |
| 2003/0120164 | A1 | 6/2003 | Nielsen et al. |
| 2003/0163355 | A1 | 8/2003 | Kaiser et al. |
| 2004/0034284 | A1 * | 2/2004 | Aversano et al. ............ 600/300 |
| 2004/0073126 | A1 | 4/2004 | Rowlandson |
| 2004/0243446 | A1 | 12/2004 | Wyatt |
| 2005/0060198 | A1 | 3/2005 | Bayne |
| 2005/0177050 | A1 | 8/2005 | Cohen |
| 2006/0271409 | A1 | 11/2006 | Rosenfeld et al. |
| 2007/0191721 | A1 | 8/2007 | Parker |
| 2007/0201676 | A1 * | 8/2007 | Gillis et al. ............ 379/265.01 |
| 2009/0055220 | A1 * | 2/2009 | Rapaport et al. ............ 705/2 |

FOREIGN PATENT DOCUMENTS

| | | |
|---|---|---|
| JP | 2004157930 A | 6/2004 |
| WO | 99/55227 | 11/1999 |
| WO | 00/30529 | 6/2000 |

OTHER PUBLICATIONS

"MUSE Cardiology Information System Heart of the New MUSE Generation," 8 pgs., http:www.gehealthcare.com/euen/cardiology/docs/MUSE_brochure_e.pdf, printed Apr. 2, 2009.

"ECGenius MUSE Cardiology Information System," 12 pgs., http:www.gehealthcard.com/usen/cardiology/diagnostic_ecg/docs/ECGenius.pdf, printed Apr. 2, 2009.

"MobileLink Wireless Communications for ECG," 6 pgs., http:www.gehealthcare.com, printed Apr. 2, 2009.

U.S. Appl. No. 11/026,330, filed Dec. 30, 2004, entitled "Medical Device Information System."

U.S. Appl. No. 11/022,342, filed Dec. 23, 2004, entitled "Providing Data Destination Information to a Medical Device."

* cited by examiner

SELECTIVELY ROUTING PATIENT DATA BETWEEN FIELD DEVICES AND TREATMENT CENTER DESTINATIONS

This application claims the benefit of U.S. Provisional Application Ser. No. 61/067,591, filed Feb. 29, 2008, the entire content of which is incorporated herein by reference.

TECHNICAL FIELD

The invention relates to transmitting patient data from the scene of an emergency event to a treatment center, and more particularly, to techniques for routing patient data from remote field devices to various destinations associated with a network of patient treatment centers.

BACKGROUND

In the context of a medical emergency, a patient is often first treated in the field by a first responder, such as police or fire department personnel, and/or a paramedic, such as an advanced cardiac life support (ACLS) certified paramedic associated with a local emergency medical service (EMS). In the field, the patient may be diagnosed and/or treated using a medical device, such as an external defibrillator, which may include patient physiological monitoring capabilities. The patient may then be transported to a hospital or other treatment center for further and, in some cases, more elaborate and critical treatment. In general, it is desirable that such further treatment at the hospital be provided as quickly as possible.

For example, Acute Coronary Syndrome (ACS), which includes Acute Myocardial Infarction (AMI), is responsible for half of all deaths related cardiovascular disease. Approximately one third of patients with confirmed ACS are diagnosed with ST-segment Elevation Myocardial Infarction (STEMI). One type of treatment performed at a hospital for a patient diagnosed with STEMI is a procedure called Percutaneous Coronary Intervention (PCI), commonly known as coronary angioplasty. The procedure involves inserting a balloon catheter into a patient's clogged artery and expanding the balloon in an attempt to open up a passage for blood flow within the clogged artery. PCI can be an effective treatment for STEMI patients provided that the treatment is quickly delivered to the patient. The longer that the flow of blood to the heart is blocked, the higher the risk of serious damage to the heart muscle. Thus, reducing the time interval between onset of ACS and PCI treatment is critical to reducing the mortality rate for STEMI or other ACS patients.

In many cases, when a patient first begins to experience symptoms of ACS, several events must take place before PCI or some other critical in-hospital treatment can be administered to the patient. For example, the paramedics may be called and need to arrive at the scene. The patient may be monitored using an external defibrillator. This may involve acquiring and displaying an electrocardiogram (ECG), e.g., a 12-lead ECG, from the patient, and analyzing the results. Other physiological parameters of the patient, such as oxygen saturation, blood pressure, or carbon dioxide partial pressure, may be monitored with the defibrillator or one or more other medical devices.

The defibrillator may provide an indication that the patient is experiencing or suspected to be experiencing STEMI or some other AMI, or allow a user to make such a determination, based on analysis of the ECG. The defibrillator may also determine, or allow a user to determine, that the patient is experiencing an arrhythmia, such as ventricular fibrillation, based on the ECG. If the patient is experiencing an arrhythmia, the defibrillator may deliver one or more electrical defibrillation shocks to terminate the arrhythmia.

SUMMARY

In general, the invention is directed to techniques for routing medical event data from a field device that at least one of monitors or treats a patient in the field, such as an external defibrillator, to a selected subset of a plurality of possible destinations. The event data may include physiological data of the patient, such as a 12-lead electrocardiogram (ECG). Each of the destinations is associated with one of a plurality of patient treatment centers, and may include, as examples, computing device, printers, displays, personal digital assistants, or web-accessible accounts.

In some embodiments, a server maintains information or rules for at least some of the destinations used by the server for determining whether event data received from a field device is routed to the destination. The information or rules may be user-configurable. In some cases, the server may also make the routing determination based on an analysis of event data, such as determination as to whether the event data includes a 12-lead electrocardiogram (ECG) or indicates that the patient is suspected to be experiencing an acute myocardial infarction. For example, an event data filtering rule for at least some destinations may specify that the destination receives all event data, only event data with a 12-lead electrocardiogram (ECG), or only event data that indicates that the patient is suspected of having suffered an acute myocardial infarction (AMI).

In some embodiments, the server selects a subset of the destinations for receipt of the event data based on destination location information for each of the destinations and one or more location rules. For example, according to a location rule, the server may select a treatment center based on at least one of proximity or travel time from the field device to the treatment center, and route event data to destinations associated with the selected treatment center. As another example, the server may select a physician based on at least one of proximity or travel time to a treatment center, and route the event data to a destination associated with the selected physician.

In some embodiments, the server selects a subset of the destinations for receipt of the event data based on scheduling information for each of the destinations. In particular, the server may determine whether destinations are available based on the scheduling information for the destination, and route destination information to available destinations. For example, the server may route event data to a destination that is associated with a physician, such as a personal digital assistant (PDA) or a tablet personal computer (PC) of the physician, based on scheduling information that indicates whether the physician is on duty or on call.

In some embodiments, the server may calculate a treatment time interval for an event by collecting times from various devices associated with an EMS and patient treatment facility that treated the patient. For example, the server may retrieve a time at which paramedics were dispatched to or arrived at the patient from the EMS, and a time of a percutaneous transluminal coronary intervention from a treatment facility. The calculated interval may be used to evaluate the timeliness of patient treatment, e.g., be presented to a reviewer by the server in the form of a report, or by the server to determine to which facilities to direct a patient and which destinations to route event data.

In one embodiment, a method includes receiving, at a server, event data that comprises physiological data for a patient from a field device used to at least one of monitor or treat the patient during an event, the server storing a plurality of destination profiles associated with respective destinations, the destinations associated with patient treatment centers, at least some of the destination profiles including respective event data filtering rules. The method further includes selecting a subset of the destinations based on the event data filtering rules, and routing the event data from the server to the selected subset of the destinations.

In another embodiment, a network server comprises a memory that stores a plurality of destination profiles, each of the destination profiles associated with a respective one of a plurality of destinations that are associated with a network of patient treatment centers, wherein at least some of the destination profiles include at least one event data filtering rule for the respective destination. The server further comprises a processor that receives event data that comprises physiological data for a patient from a field device used to at least one of monitor or treat the patient during an event, selects a subset of the destinations based on the event data filtering rules, and routes the event data from the server to the selected subset of the destinations.

In another embodiment, a computer-readable medium comprises instructions that cause a programmable processor of a network server to receive event data that comprises physiological data for a patient from a field device used to at least one of monitor or treat the patient during an event, the server storing a plurality of destination profiles associated with respective destinations, the destinations associated with patient treatment centers, at least some of the destination profiles including respective event data filtering rules. The medium further comprises instructions that cause the programmable processor to select a subset of the destinations based on the event data filtering rules, and route the event data from the server to the selected subset of the destinations.

In another embodiment, a system for managing communication of patient data within a regional patient treatment network that includes at least one emergency medical service and a plurality of patient treatment centers comprises a plurality of field devices associated with the emergency medical service, and a plurality of destinations, each of the destinations associated with at least one of the patient treatment centers. The system further comprises a network server that stores a plurality of destination profiles, each of the destination profiles associated with a respective one of the plurality of destinations, wherein at least some of the destination profiles includes at least one event data filtering rule for the respective destination, receives event data that comprises physiological data for a patient from one of the field devices used to at least one of monitor or treat the patient during an event, selects a subset of the destinations based on the event data filtering rules, and routes the event data to the selected subset of the destinations.

In another embodiment, a method includes identifying at least one emergency medical system (EMS) and a plurality of patient treatment centers within a geographical region, forming a regional patient treatment network comprising the EMS and patient treatment centers, and receiving subscriptions from the EMS and patient treatment centers to a patient data communication service for the regional patient treatment network. The method further comprises routing patient data between devices associated with the EMS and devices associated with the patient treatment centers with the server based at least in part on user-configurable information stored within the server and an analysis of physiological data included within the patient data.

The term emergency medical system is used interchangeably in this disclosure with the term emergency medical services (EMS), and may include ambulance services, life squads, rescue squads, first aid squads, first responders, referring hospitals, treatment centers, or any other service or entity associated with the treatment of those in need of urgent medical care. In some examples, a field device may be any device used for or during pre-hospital treatment or monitoring of a patient, and may be referred to as a pre-hospital device. Event data collected by a field device may be referred to as pre-hospital data.

Embodiments of the invention may provide one or more advantages. For example, use of an Internet Protocol network to facilitate communication between EMS field devices and patient treatment facility destinations, as opposed to point-to-point communication, may allow the information to be distributed to multiple locations. Furthermore, embodiments that store user-configurable rules or other information for a plurality of destinations, and route event data to a selected subset of the destinations based on stored information, may ensure that the destinations receive relevant or desired data, and do not unnecessarily receive event data. Additionally, some embodiments may facilitate delivery of event data to the most relevant destinations in terms of location, availability, and type of treatment offered based on location or scheduling information retrieved for the destinations.

If a patient is transported from the field to a treatment center that does not have the necessary facilities or staff to treat the patient, or is not ready for the patient, delivery of critical treatment may be delayed. For example, if a patient experiencing STEMI or other ACS is transported to a treatment center does not have a catheterization lab or an available cardiologist, the patient will need to be rerouted from the initial treatment center to another treatment center having the proper facilities and available staff. Once the patient arrives at a treatment center having PCI capabilities, patient demographic data and insurance information may need to be collected by the in-processing staff, the catheterization lab needs to be activated, a cardiologist needs to be located, and further diagnosis of the electrocardiogram by the cardiologist may be required. If a cardiologist is not on-site, the nearest on-call cardiologist may need to be located and contacted. Embodiments that deliver relevant event data from a field device to a plurality of relevant treatment facility destinations may improve the timeliness of delivery of a critical therapy to the patient at a treatment facility, e.g., improve the door-to-balloon time for catheterization of ST-Elevated Myocardial Infarction (STEMI) patients.

DETAILED DESCRIPTION

Figure 1:
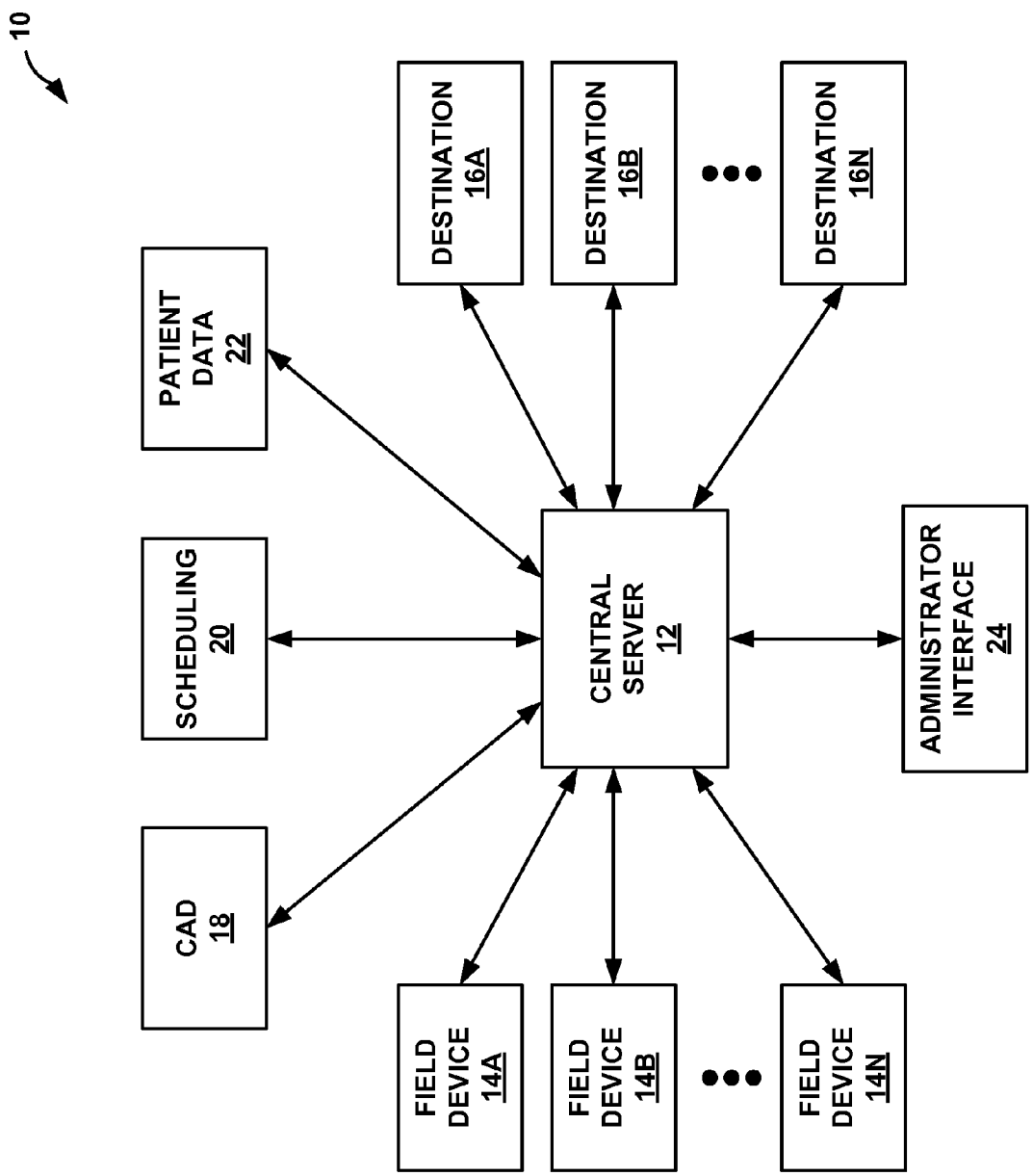
FIG. 1 is a block diagram illustrating an example data transport system that includes a central server configured to route medical event data in accordance with the techniques of this disclosure.

FIG. 1 is a block diagram illustrating an example medical event data transport system 10 that includes a central server 12. In the illustrated example, data transport system 10 includes central server 12, field devices 14A-14N (collectively, "field devices 14"), destinations 16A-16N (collectively, "destinations 16"), computer-assisted dispatch (CAD) module 18, scheduling server 20, patient data server 22, and administrator console 24. In general, data transport system 10 provides an infrastructure for transporting medical event and other patient data between a plurality of field devices 14 and destinations 16.

Central server 12 routes event data received from field devices 14 to various, selected subsets of destinations 16 based on user-configurable filtering rules or other information stored within the central server. Central server 12 may be connected to the Internet, and utilize a secure internet protocol for communication with the other devices and servers within data transfer system 10. Although illustrated as a single server 12, server 12 may comprise any number of servers, computing devices, or data storage devices that cooperate to provide the functionality attributed to central server 12 herein. Such devices may be located in a server farm, as one example, or they may be geographically distributed.

In between the central server 12 and any one or more of the field devices 14 there may be any number of gateways (not shown in FIG. 1) that provide a connection to the Internet for the field devices. Likewise, gateways (not shown in FIG. 1) may also be placed between central server 12 and one or more of the destinations 16. Central server 12 may include a web server that includes a web interface to present information to and collect information from an administrator logged into the system via administrator interface 24 and/or other users logged in at destinations 16. The administrator, or other users associated with individual destinations 16, may log onto server 12 and modify routing rules, filtering rules or other information stored by the server, in order to configure the server to route particular medical event data to a specific destination.

Field devices 14 are provided for monitoring patient physiological symptoms and/or collecting patient and event data. Each field device 14 may include any of a number of physiological monitoring devices and data collection devices. Field devices 14 may also provide patient therapy.

Example field devices 14 include an external defibrillator, a combined defibrillator/monitor, a standalone monitor, a 12-lead electrocardiograph, a perfusion sensor, a carbon-dioxide ($CO_2$) sensor, a thermometer, or the like. In addition, field devices 14 may include personal digital assistants (PDAs), tablet personal computers (PCs) or other non-therapeutic, non-monitoring data collection devices and, in any case, may receive user input from emergency medical service (EMS) personnel. For example, EMS personnel may enter data such as a diagnosis or description of a patient's condition via a user interface on a PDA, a tablet PC, a defibrillator/monitor or other data collection device. In addition, the EMS personnel may enter patient demographic information, such as the patient's name, medical history, insurance information, or other identifying information. In this manner, a field device 14 may collect and transmit patient physiological data as well as other patient and event data to central server 12. In addition, field devices 14 may include be integrated with Electronic Patient Care Reporting (ePCR) software or products to collect and transmit patient demographic information. The term emergency medical services (EMS) includes any service or entity associated with the treatment of those in need of urgent medical care and/or the provision of out of hospital acute care, and may include, as examples, ambulance services, life squads, rescue squads, first aid squads, paramedic services, or first responders.

Although, for ease of illustration, the field devices 14 are illustrated in an identical manner in the block diagram of FIG. 1, the field devices 14 need not be identical and may include a variety of different devices. For example, field devices 14 within a data transport system 10 may include several defibrillator/monitors, several PDAs, several $CO_2$ sensors, etc. Each of field devices 14 may include any number of physiological monitoring, therapy delivery, and data collection elements and, thus, may facilitate any one or more of physiological monitoring, therapy delivery and data collection.

Each field device 14 may transmit medical event data to central server 12 through a secure internet protocol. In some embodiments, field devices 14 may transmit the event data to a gateway using a wireless personal area network (PAN) such as a network designed in accordance with the Bluetooth® specification, or by means of a cabled connection. A variety of gateway types and transmission links may be used within a single data transport system 10. In some embodiments, the gateway transmits the event data to central server 12 over a Mobile Internet Protocol (IP) network, which may utilize a cellular telephone network infrastructure.

For example, a gateway may include a cellular telephone, a personal digital assistant (PDA), or a tablet personal computer (PC) that is attached to a field device 14 or carried by the EMS personnel who uses the field device. The gateway may receive medical event data from the field device, and software installed onto the gateway may transmit the event data over a secure internet protocol to the central server 12. In some embodiments, field devices 14 may directly transmit event data to server 12 via such a network and utilizing such a protocol, i.e., without the need for a gateway.

Central server 12 receives medical event data from field devices 14, and routes the event data to a selected subset of destinations 16. When the event data is received at a destination 16, the destination may print a report, generate an audible notification, send an e-mail notification to a user, analyze the data, receive comments, forward the data and comments to another destination, or enable a user to view or print reports. Destinations 16 may include specific devices associated with the one or more patient treatment centers, such as computing devices, displays, printers, cellular telephones, or PDAs. Furthermore, destinations 16 may include web-accessible accounts, such as an email account, which may allow a user to retrieve event data routed to such a destination at a later, more convenient time.

Destinations 16 may be associated with patient treatment centers, e.g., hospitals, clinics, hospital networks, or practice groups. Destinations 16 may also be associated with individuals who are associated with treatment centers, and thereby associated with treatment centers. A destination 16 associated with an individual person, such as a cardiologist or other physician, may include a cellular telephone, PDA, or tablet PC used by that cardiologist or physician. Other example destinations 16 associated include a printer or receiving station at a patient treatment center. Destinations 16 may also be classified as physical or logical. A physical destination refers to a physical device, such as a printer, receiving station, cellular phone, or the like. A logical destination refers to an account or virtual device that does not have hardware or a physical medium, such as an email or other web-accessible account, as examples.

Although, for ease of illustration, the destinations 16 are illustrated in an identical manner in the block diagram of FIG. 1, the destinations 16 need not be identical and may include a variety of different devices. For example, destinations 16 within a data transport system 10 may include several printers, several receiving stations, several PDAs, several cell phones, several e-mail accounts, etc.

A treatment center, such as a hospital, may be associated with multiple different destinations 16. For example, a treatment center may have separate destinations for the billing department, the record keeping department, the emergency department (ED), the scheduling department, specialty labs such as a catheterization lab, and physicians who are on-duty or on-call. In some embodiments, one or more administrators can modify event data filtering rules or other rules or information within the central server 12 to configure the type and format of event data that should be routed to some or all of the various destinations within system 10. An administrator associated with a regional network of treatment centers may modify such rules or information for destinations associated with multiple treatment centers, or administrators for each treatment center may each modify such rules or information for the destinations associated with its own treatment center. In some embodiments, one or more of the users of the different destinations 16 can modify event data filtering rules or other information within the central server to configure the type and format of medical event data that should be routed to its associated destination 16.

Based on such user-configured rules and information, central server 12 routes medical event data to destinations 16. For example, according to event data filtering rules or other information stored within central server 12, a record keeping destination 16 for a treatment center or regional network may receive all medical event data from a field device 14. As another example, according to event data filtering rules or other information stored within central server 12, a catheterization lab may only receive a subset of the event data from field device 14, and receive the subset of event data only if the patient is suspected of having suffered an acute myocardial infarction (AMI).

Data transfer system 10 may enable different EMS services, pre-hospital services, treatment centers, hospitals, specialty care centers, such as percutaneous coronary intervention (PCI), catheterization centers, or level-1 trauma centers, and care providers to form a common regional network of medical services, efficiently route medical event data within the common regional network, and provide patient intervention in a timely manner. Although generally described herein in the context of a single network, e.g., a regional network of EMS and patient treatment centers, server 12 may enable communication for a plurality of such networks in a plurality of geographically distributed regions. Server 12 may be maintained, and the services provided via server 12 provided by, an entity other than the EMS, treatment centers, or regional network. For example, a third party, such as a manufacturer of field devices 14 or destination devices 16, may maintain server 12 and provide services to support users of the server and data transport services.

Computer-aided dispatch (CAD) module 18 provides dispatch information and travel information to central server 12. For example, CAD module 18 may provide information that allows data transmission to appropriate destinations 16, e.g., destinations 16 associated with appropriate treatment centers, depending on the time of day and traffic route time. CAD module 18 may provide this information in response to a request from central server 12.

Scheduling server 20 stores scheduling information associated with destinations 16, which may be accessed and retrieved by central server 12. Scheduling information may include information relating to when a destination user, such as a physician or cardiologist, is "on call" or "on duty." Scheduling information may also include information relating to whether a particular facility, such as a catheterization lab, is open, occupied, or available. Scheduling server 20 may provide scheduling information to central server 12 in response to a request from central sever 12. In some embodiments, central server 12 may store scheduling information for the various destinations 16 based on information received from scheduling server 20. Central server 12 may periodically poll scheduling server 20 for such information. Scheduling server 20 may comprise one or more servers that maintain personnel, room and resource schedules for one or more hospitals or other treatment centers associated with the data transfer system 10.

Patient data server 22 stores historical patient records and patient demographic data for one or more patients. The patient records and demographic data may be associated with patients who have been treated in the past by one of the hospitals or other treatment centers associated with the data transfer system 10. Patient data server 22 may store patient information and transmit historical patient records to central server 12 in response to a request from central sever 12. Then, central server 12 may compare current patient data with historical patient data and route event data to particular destinations 16 based on the comparison.

For example, central server 12 may compare a current ECG transmitted by a field device 14 as medical event data to a past ECG for that same patient retrieved by patient data server 22. The comparison may assist central sever 12 in determining whether the patient is suffering from an acute myocardial infarction (AMI). Central server 12 may use the comparison to make a routing decision for the ECG and other medical event data.

CAD module 18, scheduling server 20, and patient data server 22 may be integrated on the same platform as central server 12 or may be implemented on separate servers. If implemented on separate servers, each of these severs may communicate with the central server over a secure internet connection. Any two or more of the CAD module 18, scheduling server 20, patient data server 22 and central server 12 may be integrated on the same platform.

Figure 2:
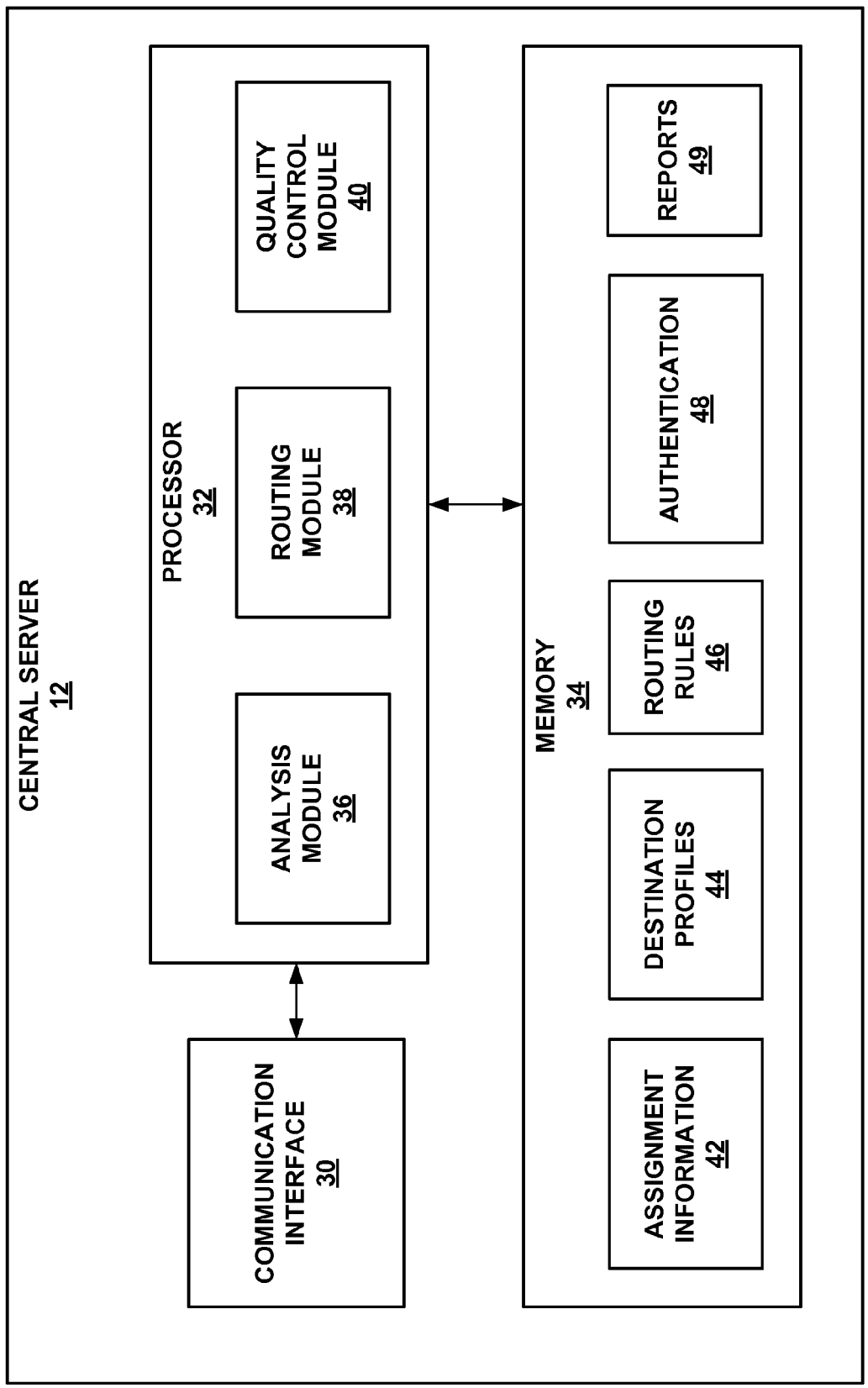
FIG. 2 is a block diagram illustrating an example configuration of the central server of FIG. 1.

FIG. 2 is a functional block diagram illustrating central server 12 in further detail. Central server 12 includes a communication interface 30, a processor 32, and memory 34. Communication interface 30 may provide connectivity to the Internet for central server 12 through a secure internet protocol in order to facilitate communication between central server 12 and the other devices and servers within data transfer system 10.

Communication interface 30 receives medical event data from field devices 14. Communication interface 30 sends the medical event data to a selected one or more destinations 16 within data transfer system 10. Communication interface 30 may receive instructions from a routing module 38 of processor 32 indicating which destinations 16 should receive event data and, in some examples, a particular format for the event data. The medical event data may include physiological data, such as an ECG for example. In order to ensure data integrity, communication interface 30 may append a Cyclic Redundancy Check (CRC) code to the event data prior to transmitting event data to destinations 16, and may check an appended CRC code, e.g., applied by field device 14 or associated gateways, prior to receiving event data at central server 12.

Processor 32 may provide status information to field devices 14 transmitting information to central server 12 indicating that any transmissions or communications were successfully received and processed by the destinations 16. Processor 32 may provide e-mail notifications to an administrator when a failure to communicate is detected. Communication interface 30 also exchanges information with CAD module 18, scheduling server 20, and patient data server 22 via a secure internet communications protocol.

Processor 32 may provide a web-based graphical user interface to present information to and receive input from an administrator via administrator interface 24 (FIG. 1) or users of destinations 16 via communication interface 30. The web-based graphical user interface may receive configuration information. The configuration information may be information that is associated with a destination 16, such as location information, scheduling information, event data filtering rules, and formatting information. When communication interface 30 receives configuration information for the destination, communication interface 30 may send the information to processor 32, which may create or update a destination profile 44 associated with the destination 16 and store the created or updated destination profile in memory 34. Configuration information may also include information configuring routing rules 46 stored in memory 34, which need not be specific to any particular destination 16, e.g., may be applied to the information in destination profiles 44 for any destination 16.

Processor 32 may provide an individual login for each user of the system and the capability to define roles that assign specific privileges to each user. In this manner, access can be limited to only the features and information that a user is authorized to use or receive. Furthermore, destinations 16 that receive patient information may be required to authenticate with server 12 through authorization measures, such as user IDs, passwords or digital certifications, before any medical event data is passed to them for printing or viewing. Processor 32 may store user or device names, passwords, encryption keys, and digital certifications, as well as information defining roles and privileges for users, in authentication module 48 of memory 34.

Central server 12 may store accounts in order to efficiently manage the various users and devices of data transfer system 10. Accounts may be used by organizations, such as EMS networks or treatment center networks, to organize and manage devices and destinations within the organization's control. The accounts may be classified as transmitting accounts, receiving accounts, and transmitting/receiving accounts. A transmitting account manages only field devices 14, and a receiving account manages only destinations 16. A transmitting/receiving account may manage and control both field devices 14 and destinations 16. Receiving accounts and transmitting/receiving accounts can control the field device accounts from which they wish to receive patient information. Transmitting accounts and transmitting/receiving accounts may configure the receiving accounts to which they wish to have data routed. In order to prevent long-term data storage within central server 12, account administrators for each customer have the ability to specify the length of time that data associated with their accounts is stored.

Processor 32 includes optional analysis module 36, routing module 38, and optional quality control module 40. Processor 32 is coupled to communication interface 30 and memory 34. Processor 32 may receive instructions from memory 34 or from another data storage system that execute on the processor and cause the processor to perform the functions described herein with respect to the processor or central server 12. Processor 32 and the various modules 36, 38 and 40 of processor 32 may be provided as hardware, firmware, software, or any combination thereof. Processor 32 may include one or more physical processors, e.g., microprocessors, or digital signal processors (DSPs), within in one or more physical devices.

Memory 34 may store assignment information 42, destination device information 44, routing rules 46, authentication information 48, and reports 49. Memory 34 may also store instructions executed by processor 32 to cause processor 32 and server 12 to provide the functionality ascribed to them herein. Memory 34 may be any sort of volatile or non-volatile data storage device, such as random access memory (RAM), read-only memory (ROM), electronically-erasable programmable ROM (EEPROM), a hard disk drive, or the like.

In examples that include analysis module 36, the analysis module analyzes medical event data that is received from field devices 14. Medical event data may include physiological data collected from a monitoring device. Examples of physiological data include a 12-lead ECG or other ECG, carbon dioxide ($CO_2$) data, perfusion sensor data, patient temperature data, glucose monitoring data, or some combination thereof Medical event data may also include data entered into a field device by EMS personnel such as a diagnosis or description of the patient's condition as well as patient demographic information, such as the patient's name, medical history, or insurance information.

Analysis module 36 may perform one or more analyses on medical event data, historical patient records, or a combination of these data. Analysis module 36 may analyze the event data to determine if the event data is of a particular data type, or if the patient has a particular physiological condition. For example, one data type may be 12-lead ECG data while another data type may be perfusion sensor data. Analysis module 36 may analyze the medical event data to determine a patient condition based on the event data. For example, analysis module 36 may analyze an ECG to determine whether the patient is suspected of having suffered an acute myocardial infarction (AMI). As another example, analysis module 36 may analyze a 12-lead ECG to determine if the ECG has ST segment elevation in two or more contiguous sensor leads. Analysis module 36 may analyze a combination of physiological data received from field devices 12 and historical patient records retrieved from patient data server 22 to determine whether a patient is experiencing a particular condition.

In some examples, routing module 38 routes data to a subset of destination devices based, in part, on a result of the analysis by analysis module 36. Routing module 38 may identify a subset of the destinations based on assignment information 42 stored in memory 34. Assignment information 42 may include definitions or rules that map each field device 14 to one or more destinations 16. In cases where the destinations 16 are associated with treatment centers, assignment information 42 may include definitions that map each field device 14 to one or more treatment centers.

In one example, a field device 14 may be an external defibrillator including a 12-lead electrocardiograph, and the destinations 16 may be grouped into three groups with each group corresponding to a treatment center. One or more user-configurable transmission sites may be defined within the defibrillator. The transmission sites define where the defibrillator sends event data and may correspond to site accounts stored within central server 12. Assignment information 42 provides mappings between the site accounts within central server 12 and one or more treatment centers or individual destinations. When event data is received at central server 12 from a field device 14, routing module 38 maps the event data to one or more destinations based upon the assignment definitions. In this manner, routing module 38 identifies a subset of all the destinations registered with the central server that are allowed to receive event data from a particular field device 14.

Routing module 38 may also apply a set of routing rules 46 to further limit the subset of destinations identified by the assignment rules. Based on the application of routing rules 46, routing module 38 selects a final set of destinations to receive event data. Routing rules 46 may include location rules and scheduling rules. Routing module 38 may also apply event data filtering rules to the medical event data or a result of the analysis of the medical event data by analysis module 36 to further limit the subset of destinations. In some embodiments, event data filtering rules for each destination may be retrieved from destination information 44.

Location rules may define what destinations should receive data based on the relative location of a field device and a destination. For example, a location rule may define that event data is routed to all destinations within a twenty mile radius of the field device. Another location rule may select a treatment center that has a shortest travel time from the field device to the treatment center, and then define a further subset of destinations to include only destinations associated with the selected treatment center. Other location rules may select a treatment center having a cardiologist with a shortest travel time to the treatment center, and then include only destinations associated with the selected treatment center within the further subset of destinations. Moreover, another location rule may only select destinations associated with a treatment center that has a catheterization laboratory.

In addition, several location rules may be chained together to form a composite location rule for selecting destinations to include in the further subset. In this manner, routing module 38 may select a treatment center based on either proximity or travel time from the field device to the treatment center or from a destination user to a treatment center. Then, routing module 38 may route the event data to all destinations associated with the selected treatment center. Information regarding travel times may be retrieved by processor 32 from CAD system 18.

Scheduling rules may include, for example, a rule that certain destinations 16 only receive event data when such destinations are available (for example, a destination PDA or tablet PC associated with a cardiologist receives data only when scheduling information indicates that cardiologist is on duty or on call). As discussed above, the availability of a destination may be indicated by scheduling information for the destination, which may be stored as part of destination information 44 for the destination. Such scheduling information may be retrieved by processor 32 from a scheduling server 20, as discussed above.

Furthermore, the invention is not limited to the examples of routing rules, event data filtering rules, location information, or scheduling information described herein. Additional routing criteria stored (or acquired from another system) and used by a central server could include specific patient related information such as insurance coverage, wherein the patient and the event data is routed to an in-network facility, provider, or physician. The patient themselves or their family could request specific destinations, which may be transmitted by a field device or gateway device to a server with, or before or after, the medical event data. Such patient or insurance preference related routing information may also be retrieved by a central server from patient history records, if available on the network, e.g., from medical records system 22. Furthermore, an event data filtering rule for a destination may limit the destination to receipt of data on specific patient groups, e.g., specific insurance coverage, or specific individual patients, e.g., a physician's current patients.

Moreover, more parameters can be considered regarding a patient care center as a candidate for being physical destination. For example, the on-call cardiologist and other support staff (nursing, anesthesiologist) may be required and included in notification and decision criteria. Routing criteria can include traffic information for the location, and also for personnel attempting to get there.

During patient transport, there can be progress reports, such as expected arrival time, patient condition, etc. In addition, there can be updated information on backup candidate destinations, in case conditions change during patient transport. For example, a central server can receive and use, in the location rules, an input from a traffic condition source. Such a source can be an automated service that measures traffic congestion, for example as is often provided by departments of transportation, etc.

Upon the patient's arrival, a confirmation can be sent to all the applicable destinations, physical and electronic, so that data routing will be concluded. In fact, data that has been sent only redundantly in anticipation can be then deleted, to preserve confidentiality.

Routing module 38 may format the event data according to formatting information associated with each destination in the final set of destinations, and route the formatted event data to each destination in the final set of destinations. Routing module 38 may route the data by sending instructions to communications interface 30 indicating how event data should be formatted and the destination to which the formatted data should be routed.

The formatting information for a destination may be retrieved from the corresponding destination profile 44 within the destination information 44 within memory 34. Example formatting information may include: a "grid option" that indicates the type of grid that appears on reports when they are viewed or printed from the destination (e.g., 1 mm, 5 mm, or no grid); a "show patient information option" that specifies whether sensitive patient information is included on reports when they are viewed or printed from the destination; a "twelve lead format type" that specifies the format for 12-lead reports received at the destination (e.g., 3-channel, 4-channel, or 12-channel); a "twelve lead type" that specifies the type of 12-lead reports received at the destination (e.g., Standard or Cabrera); and a "sweep speed" that indicates the horizontal time scale at which waveforms are displayed on reports received at the destination (e.g., 25 mm/sec or 50 mm/sec). The "show patient information option" may increase patient data security in data transfer system 10 by allowing an administrator or other user to configure central server 12 to not transmit patient sensitive information to certain destinations 16. As one example, an administrator or destination user can configure any e-mailed 12-lead reports to not include patient sensitive information.

Quality control module 40 calculates various metrics associated with routing decisions made by central server 12. The metrics may be stored within memory 34 for use in future routing decisions. In some embodiments, reports 49 may be generated that may be displayed to an administrator when the administrator is logged into central server 12, or delivered or presented to another evaluator, e.g., via email or web access.

The evaluator may be a registered user of system 10, or a party who is not registered as a user of system 10.

For example, quality control module 40 may collect a first time value or time stamp from a first device and a second time value or time stamp from a second device and calculate a time interval based on the first and second time values. The first and second devices may be the same device or associated with the same treatment center, or may be different devices associated with, for example, EMS and a treatment center. For example, quality control module 40 may collect a first time value ($t_1$) indicating the time at which a patient has arrived at a treatment center and a second time value ($t_2$) indicating the time when the patient has received percutaneous transluminal coronary intervention at the treatment center. Then, quality control module 40 may calculate a door-to-balloon (D2B) time associated with the treatment center based on the time values. In another example, the first time may be the time at which paramedics were dispatched to or arrived at the location of the patient, and the time interval ($t_2-t_1$) may indicate an overall time from initiation of emergency response procedures to treatment of the patient. The time interval may be stored in central server 12 for use in future routing decisions. In other embodiments, reports 49 may be generated and sent to various devices within data transfer system 10.

As discussed above, although central server 12 is shown in FIGS. 1 and 2 as a single server, central server 12 may be implemented on more than one server. For example, various functions of central server 12 may be implemented on different servers in a server farm or on various servers distributed throughout a network. Central server 12 may also include redundant servers with automatic fail-over servers in place to ensure high overall system reliability.

Figure 3:
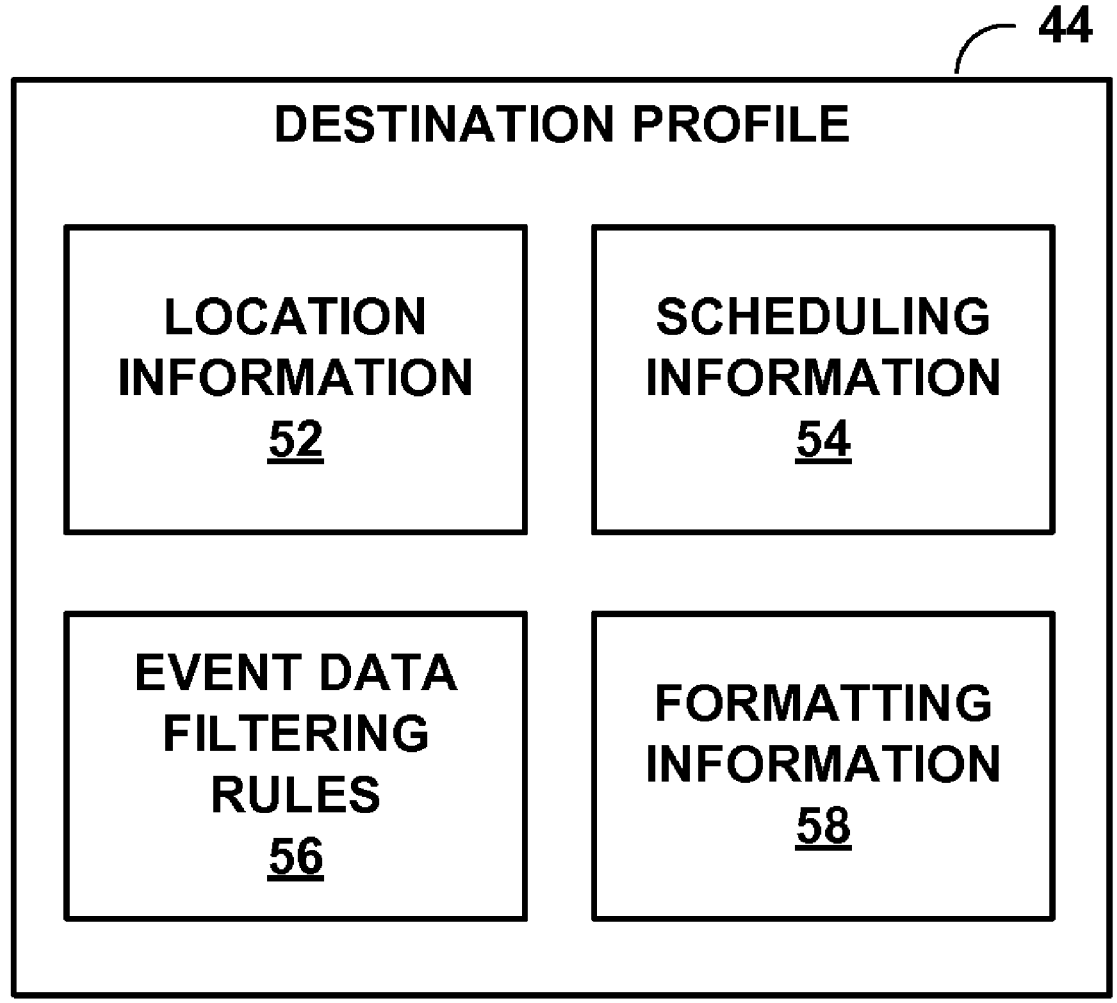
FIG. 3 is a block diagram illustrating an example destination profile that may be stored by the central server.

FIG. 3 is a block diagram illustrating an example destination profile 44 that may be stored within memory 34 of server 12. Destination profile 44 includes location information 52, scheduling information 54, event data filtering rules 56, and formatting information 58. As indicated in FIG. 2, memory 34 of server 12 may store a plurality of destination profiles 44 for a plurality of respective destinations. Destination profile 44 illustrated in FIG. 3 may be representative of the plurality of destination profiles stored by a server 12.

Location information 52 may correspond to static location data for destination devices 16 such as printers, receiving stations. In other embodiments, central server 12 may dynamically update the location information 52 by querying the appropriate destination devices 16 proximate to the time of the event. For example, when an event occurs, central server 12 may query all destination devices that are mobile, such as cellular telephones and PDAs for their current locations. The current location of a queried destination device 16 may be supplied to central server 12 by a global positioning system (GPS) unit within the destination device 16. Thus, central server 12 may use static location information as well as dynamically updated location information to route event data to various destinations based on a plurality of location rules.

Scheduling information 54 may include information indicating whether a particular user associated with the destination is "on duty" or "on call", the schedule of the user, the hours of operation of a treatment center, or other timing information that may be necessary to determine whether to route medical event data to a particular destination. Central server 12 determines whether the particular destination 16 or user is available based on the scheduling information 54 stored in the destination profile 44 for the destination. In some examples, scheduling information 54 is stored in the form of a flag or value that is updated to indicate whether or not the destination is available based upon information provided by scheduling server 20.

Event data filtering rules 56 are user-configurable for each destination 16 by an administrator or destination user. Event data filtering rules 56 determine whether a destination 16 will receive medical event data for a particular event. In some examples, the determination may be based on a result of the analysis of event data by analysis module 36.

An event data filtering rule for a destination may specify that the destination wishes to receive data only of a certain data type. For example, event data filtering rules may specify that a destination wishes to receive 12-lead ECGs, carbon dioxide (CO2) data, perfusion sensor data, patient temperature data, glucose monitoring data, all data, or some combination thereof. Another event data filtering rule may specify that a destination only wishes to receive event data that fulfills certain qualifications after analysis of patient symptoms. For example, the destination wishes to receive only 12-lead ECGs, or only event data (such as 12-lead ECGs) that indicate that the patient is suspected to be experiencing acute myocardial infarction, or only 12-lead ECGs having ST segment elevation in two or more contiguous sensor leads. Several individual event data filtering rules may be combined to form a composite event data filtering rule.

Formatting information 58 for a destination 12 specifies how the event data will be presented at the destination. For example, the formatting information may specify that a report should display all ECGs in 3-channel format. As discussed above, example formatting information may include: a "grid option" that indicates the type of grid that appears on reports when they are viewed or printed from the destination (e.g., 1 mm, 5 mm, or no grid); a "show patient information option" that specifies whether sensitive patient information is included in reports when they are viewed or printed from the destination; a "twelve lead format type" that specifies the format for 12-lead reports received at the destination (e.g., 3-channel, 4-channel, or 12-channel); a "twelve lead type" that specifies the type of 12-lead reports received at the destination (e.g., Standard or Cabrera); and a "sweep speed" that indicates the horizontal time scale at which waveforms are displayed on reports received at the destination (e.g., 25 mm/sec or 50 mm/sec).

Figure 4:
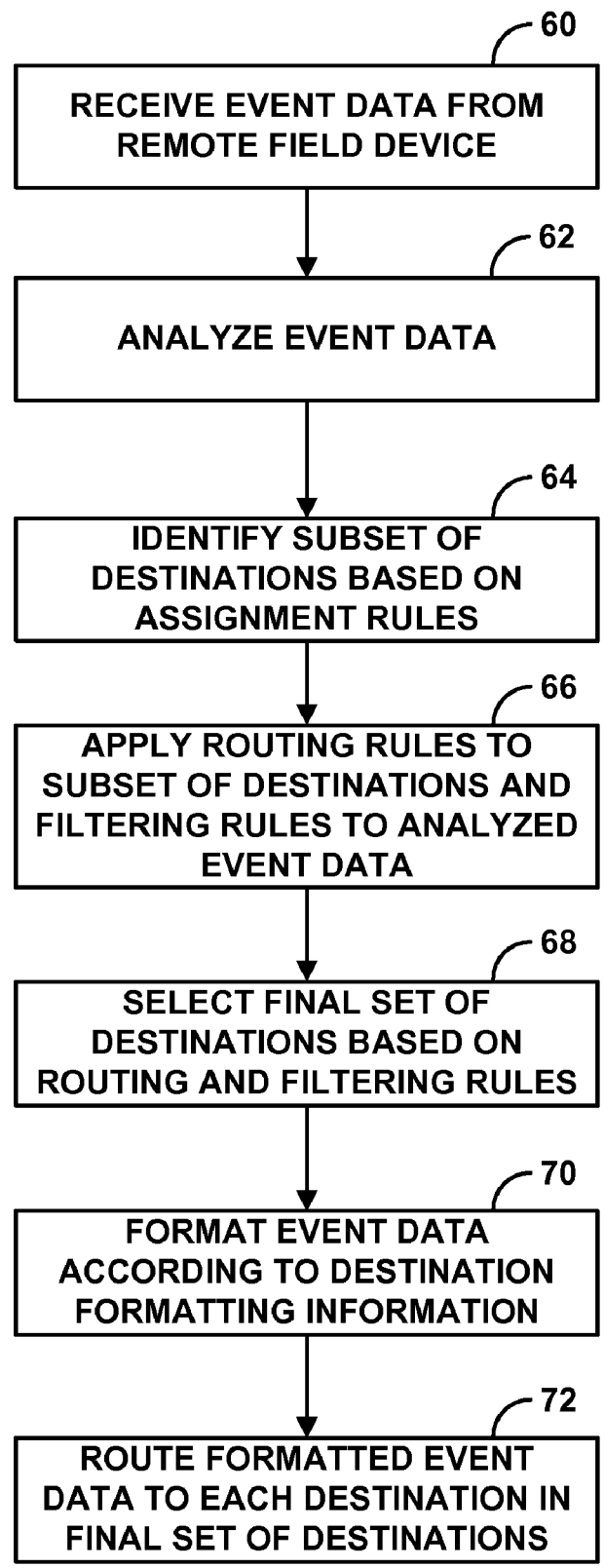
FIG. 4 is a flow diagram illustrating an example operation of a central server to route medical event data.

FIG. 4 is a flowchart illustrating an example operation of a central server, such as central server 12 of FIG. 1, to route medical event data from field devices 14 to selected destinations 16. Central server 12 receives event data from a remote field device 16 (60). The event data may include physiological data collected from a remote monitoring device as well as other patient demographic data entered by EMS personnel into a PDA or tablet PC, for example. In addition, event data may include patient demographic data collected by Electronic Patient Care Reporting (ePCR) products.

In some embodiments, central server 12 analyzes the event data (62). Central server 12 may analyze the event data to determine if the data is of a particular data type or to diagnose a particular patient condition, or both.

In other embodiments, event data may be precharacterized by the sending device as to the type of the event data. In some examples, event data may be analyzed at a field device 14 and a characterization of the data type determined based on the analysis may be sent to the central server 12 by the field device in conjunction with the event data. As one example, example, a defibrillator with monitoring capabilities may analyze a 12-lead ECG to determine if it is suspected that a patient has suffered from an acute myocardial infarction (AMI). If the defibrillator determines that a patient has suffered an AMI, the defibrillator may send an "Acute MI suspect" notification or some other notification to central server 12. The notification may be flagged by central server as analyzed data, which may be used by processor 32 to route the data according to event filtering rules as described herein.

In other embodiments, analysis module 38 of central server 12 analyzes the event data to determine a data type for routing the data according to event filtering rules. For example, analysis module 38 of central server 12 may analyze an ECG to determine whether a patient has suffered an AMI. In this manner, server 12 may route data according to event filtering rules even if it is not characterized by field device 14, or characterized with an unknown format.

Furthermore, the invention is not limited to embodiments in which the ECG is monitored or AMI is detected or indicated. In other embodiments, any physiological parameters may be monitored, and any other physiological parameter signals analyzed or characterized, to detect or indicate any other patient conditions. For example, blood pressure, respiration, oxygen saturation, electroencephalogram, partial pressure of carbon dioxide, patient neurological responsiveness, or the like may be monitored to indicate conditions, such as chronic obstructive pulmonary disease, congestive heart failure, stroke, diabetic shock, a particular type of trauma, hypothermia, contact with a poison or infectious disease, or an asthma attack.

Central server 12 identifies a subset of destinations based on assignment rules or definitions (64). The assignment rules may be retrieved from assignment information module 42 within memory 34 of central server 12. The assignment rules provide mappings between a particular field device 14 and one or more destinations 16. Central server 12 may define the identified subset of destinations 16 to include all destinations 16 associated with the field device 14 from which the medical event data was received.

Then, central server 12 applies routing rules to the identified subset of destinations 16, e.g., to the information contained within the destination profiles 44 for the identified subset of destinations (66). Central server 12 may apply location routing rules to location information 52 stored within destination profiles 44 for the subset of destinations 16, and to location information for the field device 14 or patient received from the field device with the medical event data. Central server 12 may also apply scheduling rules to scheduling information 54 stored within destination profiles 44 for the subset of destinations 16 to determine if a destination 16 or user associated with the destination is available. Central server 12 may also apply event data filtering rules 56 for the destinations 16 to the medical event data received from the field device 14, or a result of the analysis of the event data, to further limit which destinations 16 will receive event data.

Then, central server 12 selects a final set of destinations 16 based on the routing and filtering rules (68). The final set of destinations 16 may refer to the set of destinations that satisfies all of the routing rules, and for which the respective event data filtering rules are satisfied by the event data. Central server 12 formats the event data according to destination formatting information (70). For example, the destination formatting information may specify whether a report contains sensitive patient information or the type of ECG displayed on the report. Finally, central server 12 routes the formatted event data to each destination in the final set of destinations (72).

Figure 5:
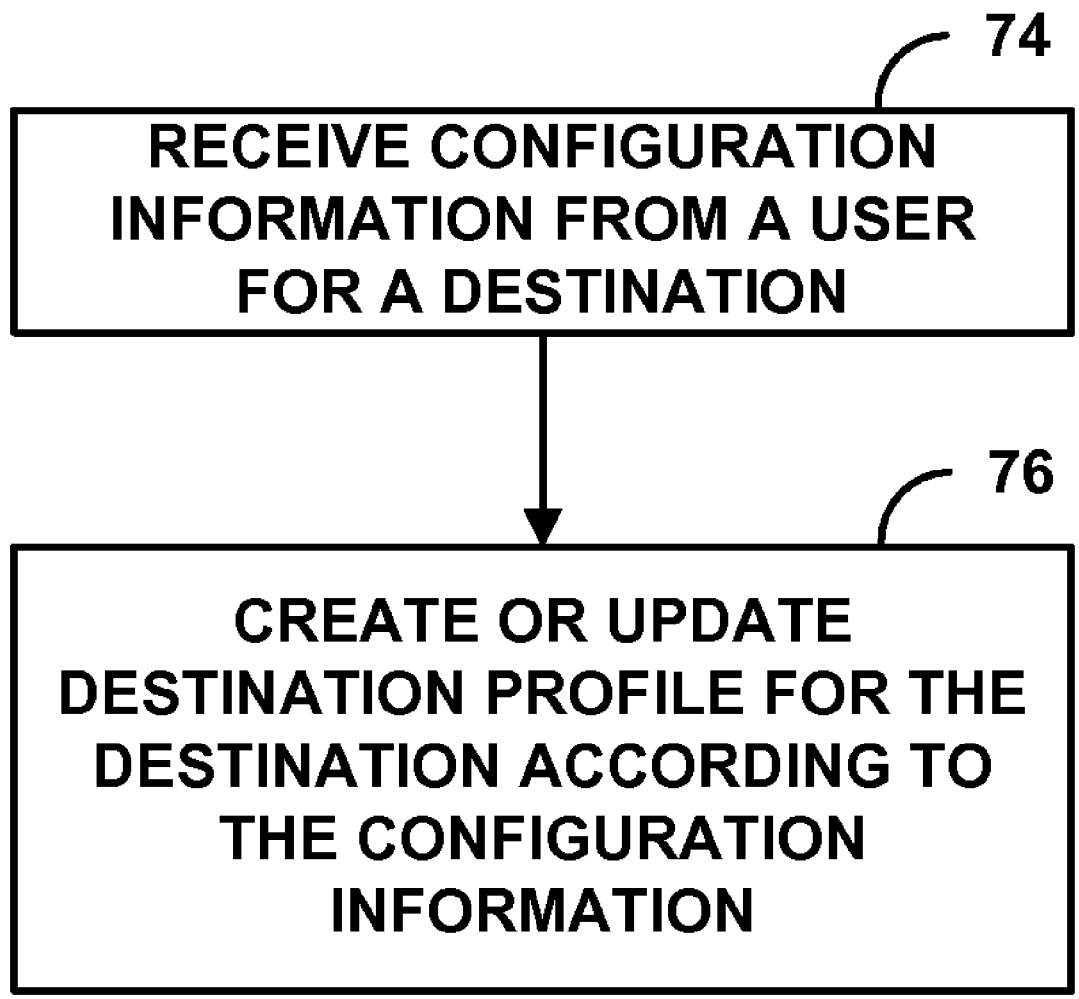
FIG. 5 is a flow diagram illustrating an example technique for user configuration of a profile for a destination.

FIG. 5 is a flow diagram illustrating an example technique for user configuration of a profile 44 for a destination 16. Central server 12 receives configuration information from a user for one or more destinations 16 (74). The configuration information may include location information, destination scheduling information, event data filtering rules, and formatting information for the destination. Central server 12 may create or update a destination profile 44 for the destination according to the configuration information (76).

Figure 6:
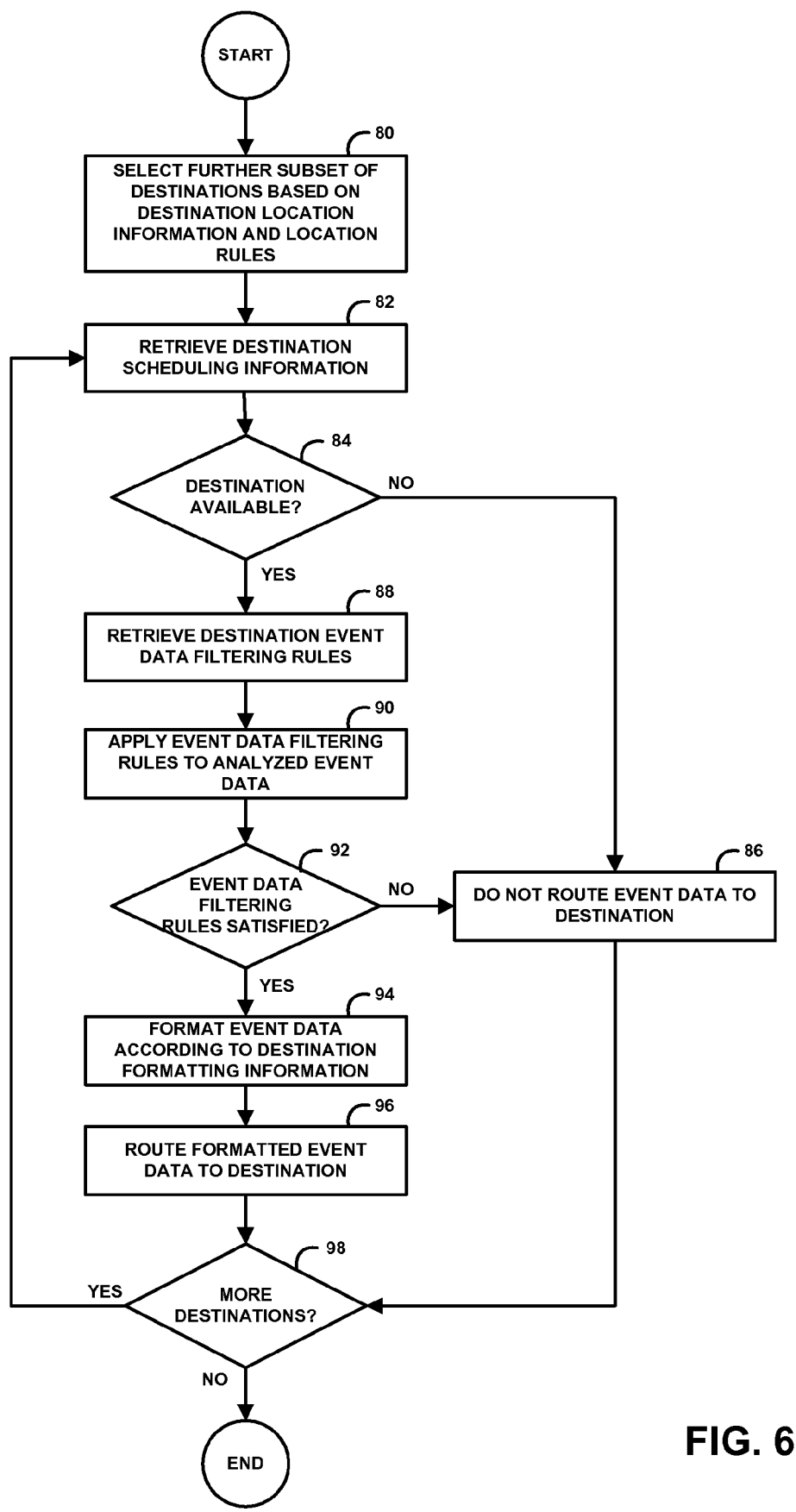
FIG. 6 is a flow diagram illustrating an example operation of a central server to route medical event data.

FIG. 6 is a flow diagram illustrating an example operation of central server 12 in greater detail. The procedure illustrated in flow diagram in FIG. 6 may be performed by routing module 38 of central server 12, which may be used to achieve steps 66-72 shown in the flow diagram of FIG. 4. Of course, other procedures could be used to achieve the same results without departing from the scope of the invention.

After central server 12 identifies the destinations associated with the field device 14 based on the assignment rules, central server 12 selects a further subset of destinations 16 based on destination location information and location rules (80). The destination location information may be retrieved from destination profiles 44 in memory 34. In other embodiments, the destination location information may be retrieved from a global positioning system (GPS) unit within the destination device 16. In this manner, central server 32 may access real time location information for a user of the destination, such as a cardiologist carrying a PDA or tablet PC.

In a similar fashion, central server 12 may analyze the event data to receive location information associated with the field device 14 from which the event data originated, or may query the field device 14 to determine a real time location of the patient. The real time location may be determined by a GPS system within the field device. In any case, central server 12 may analyze the location information for the field device and the candidate destination devices 16 to determine a destination device 16 that has a minimum distance from the field device 14, or a destination device that has a minimum travel time from the field device.

The location rules may be retrieved from routing rules 46 in memory 34 of central server 32. The location rules define what destinations should receive data based on the relative location of a field device and a destination device. For example, a location rule may define that event data is routed to all destinations within a twenty mile radius of the field device. Another location rule may select a treatment center that has a shortest travel time from the field device to the treatment center and then define a further subset of destinations to include only destinations associated with the selected treatment center. Other location rules may select a treatment center having a cardiologist with a shortest travel time to the treatment center, and then include only destinations associated with the selected treatment center within the further subset of destinations. Moreover, another location rule may only select destinations associated with a treatment center that has a catheterization laboratory. In addition, several location rules may be combined to form a composite location rule for selecting destinations to include in the further subset. In this manner, routing module 38 may select a treatment center based on either proximity or travel time from the field device to the treatment center or from a destination user to a treatment center. Then, routing module 38 may select all destinations associated with the selected treatment center.

After central server 12 has selected the destinations 16 that satisfy the locations rules, central server 12 begins to process individual destinations within the further subset of destinations. Central server 12 retrieves destination scheduling information for a particular destination (82). In some embodiments, the scheduling information may be retrieved from a destination profile 44 for the destination. In other embodiments, the scheduling information may be retrieved from scheduling server 20 in the data transfer system 10 of FIG. 1.

Scheduling information may include information indicating whether a particular user associated with the destination is "on duty" or "on call", the schedule of the user, the hours of operation of a treatment center, or other timing information that may be necessary to determine whether to route event data to a particular destination. The central server 12 determines whether the particular destination or user is available based on the scheduling information associated with the destination (84). For example, if the user is "on duty", then the user is available. If the destination is not available, central server 12 does not route event data to the destination (86) and advances to decision block (98). If the destination is available, central server 12 retrieves event data filtering rules for the destination from the corresponding destination profile stored within the server (88).

The event data filtering rules may be retrieved from the destination profile associated with the destination. The rules may be configured by an administrative user or a destination user. An example event data filtering rule might specify that the destination wishes to receive data only of a certain data type: for example, the destination wishes to receive 12-lead ECGs, carbon dioxide ($CO_2$) data, perfusion sensor data, patient temperature data, glucose monitoring data, or some combination thereof. Another example event data filtering rule may specify that the destination only wishes to receive event data that fulfills certain qualifications after analysis: for example, the destination wishes to receive only 12-lead ECG's suspect of acute myocardial infarction, or only 12-lead ECG's having ST segment elevation in two or more contiguous sensor leads. In addition, several individual event data rules may be combined together to form a composite event data rule.

Central server 12 applies the event data filtering rules to the analyzed event data (90) and determines whether all of the event data filtering rules are satisfied (92). If at least one of the event data filtering rules is not satisfied, central server 12 does not route event data to the destination (86) and advances to decision block (98). If all of the event data filtering rules are satisfied, central server 12 formats the event data according to the formatting information stored within the destination profile (94) and routes the formatted event data to the destination (96).

The formatting information may be retrieved from the destination profile associated with the destination and stored within the destination device information 44 of memory 34. For example formatting information may include a "show patient information option" that specifies whether sensitive patient information is included on reports when they are viewed or printed from the destination; or a "twelve lead format type" that specifies the format for 12-lead reports received at the destination (e.g., 3-channel, 4-channel, or 12-channel).

Central server 12 determines if there are more destinations within the further subset of destinations determined in step 80 (98). If there are additional destinations, the central server 12 retrieves scheduling information for the next destination (82). Central server repeats steps 82-98 until there are no additional destinations within the further subset of destinations for the next repeats steps 82-98 for each destination. Otherwise, if there are no additional destinations, central server ends the procedure. In this manner, central sever 12 routes data to destination devices based on event data filtering rules that are user-configurable for each destination.

In some embodiments, a destination 16 may provide a confirmation of receipt of the event data to server 12, and/or confirms or acknowledges that preparations to receive and treat the patient are underway, in response to the event data. Medical facility personnel, such as a cardiologist, receiving event data or a notification via a cellular telephone, PDA, or other mobile destination 16, may confirm that they are in route to the medical facility. Server 12 may forward such confirmations to the transmitting field device 14. Furthermore, server 12 may reroute the event data to other destinations in the case of lack of confirmation from one or more destinations, e.g., to a different facility or different personnel.

Additionally, the invention is not limited to a single transmission of event data or transmission at a single time. Prior to an during patient transport to a medical facility, event data, which may include patient condition updates, e.g., new physiological data, expected arrival times, or actual arrival at the medical facility, may be transmitted to server 12 by a field device 14, and forwarded to destinations as described herein. Furthermore, server 12 may receive updates from medical facility personnel not located at the medical facility as to expected arrival time, and forward such updates to destinations 16 at the medical facility. Server 12 may divert the patient and any current or previously transmitted event data to other destinations based on new information, such as indications that a facility or personnel are not available, traffic conditions have changed, or the patient condition has changed.

Figure 7:
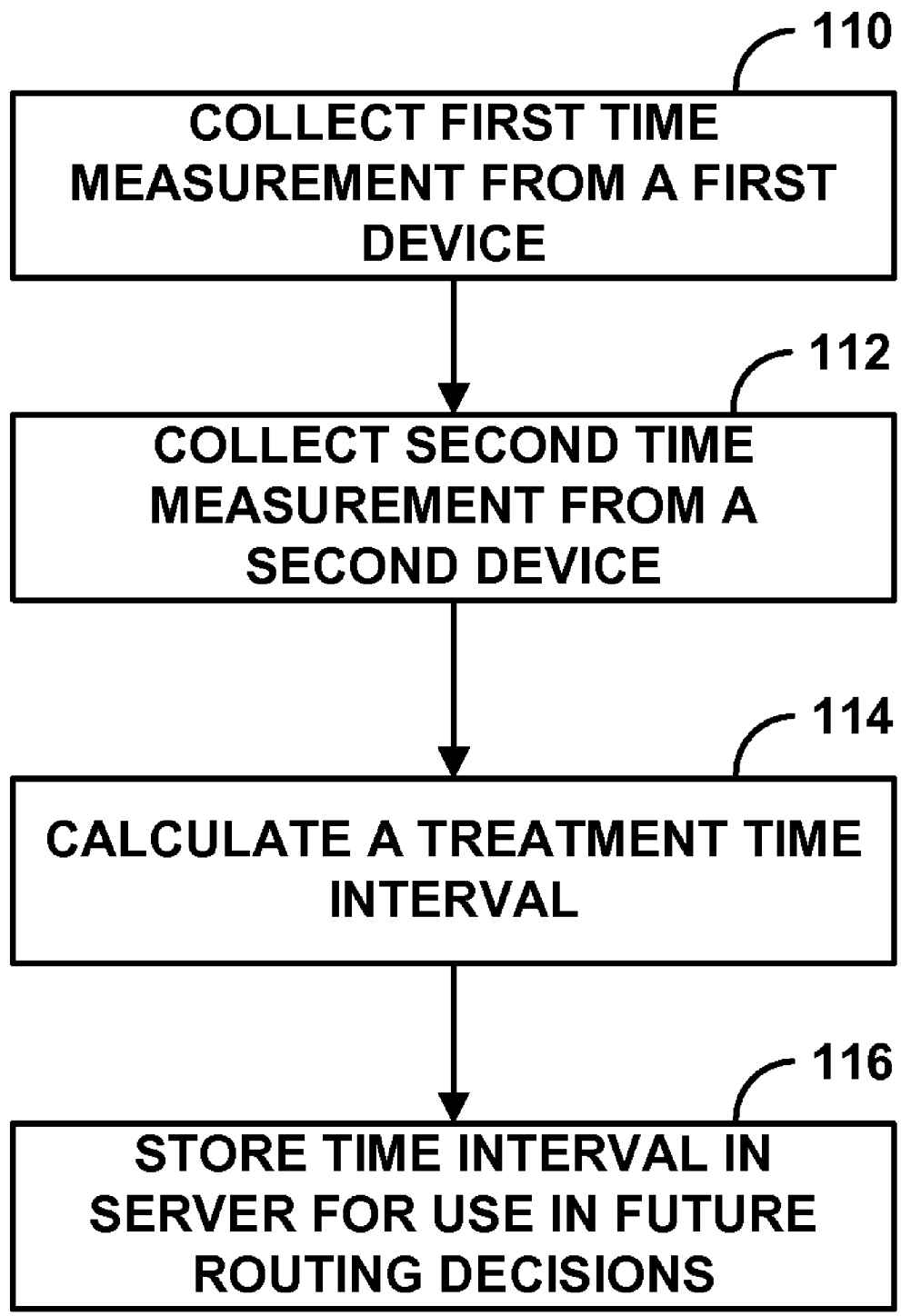
FIG. 7 is a flow diagram illustrating an example operation of a quality control and evaluation module.

FIG. 7 is a flow diagram illustrating an example operation of quality control module 40. Quality control module 40 collects a first time $t_1$ from a first device (110). In one example, quality control module 40 may collect the time at which information regarding the patient is first received at the central server from a field device. In another example, quality control module 40 may receive event data from the field device that specifies the time when the paramedics arrived at the scene or the time when the patient first called the EMS.

Quality control module 40 then collects a second time $t_2$ from a second device (112). For example, quality control module 40 may collect the time at which a patient receives catheterization treatment at a treatment center associated with the destination device. Then, quality control module 40 calculates a treatment time interval for the emergency event (114). The treatment time interval may be calculated by subtracting the first time value from the second time value, i.e., $\Delta T=(t_2-t_1)$. Finally, quality and control module 40 stores the time interval $\Delta T$ in memory 34 of server 32 for use in future routing decisions (116).

In other embodiments, the first and second device may be the same device or associated with the same treatment center. For example, quality control module 40 may collect a first time value or time stamp from a destination device relating to the time at which the patient arrived at the treatment center and a second time value or time stamp from the same destination device relating to the time at which the patient received percutaneous transluminal coronary intervention. Then, quality control module 40 may calculate a door-to-balloon (D2B) time associated with the treatment center based on the time values. Finally, quality control module 40 may store the door-to-balloon time for the treatment center to use in future routing decisions.

Figure 8:
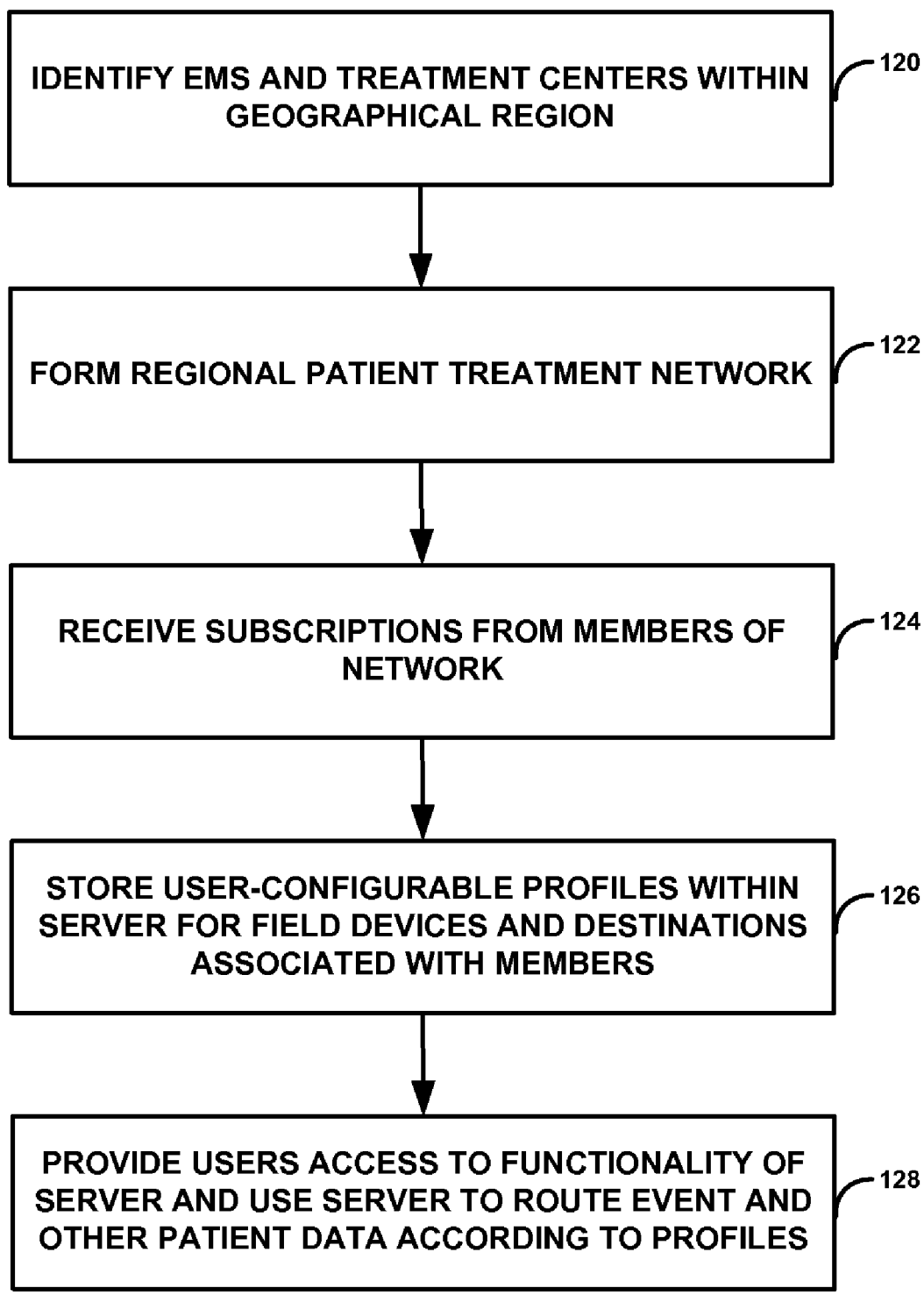
FIG. 8 is a flow diagram illustrating an example method for providing service to a regional patient treatment network using central server.

FIG. 8 is a flow diagram illustrating an example method for providing service to a regional patient treatment network using central server. First, an entity that maintains and provides services via server 12 identifies EMS providers and treatment centers within a geographical region (120). Then, the EMS providers and treatment centers forms a regional patient treatment network, which process may be guided by the entity, e.g., third party (122). The entity receives subscriptions from members of the network (124). The subscriptions may be priced based on a level of access or control, or use, e.g., bandwidth usage or number of data transmissions.

Based on the subscription, the entity configures central server to store user-configurable profiles within the server for field devices and destinations associated with members of the newly-formed network (126). Finally, the entity provides users within the network with access to functionality of the server, e.g., provides user names and passwords to facilitate user configuration of assignment information, destination information and routing rules (128). This may also include providing software that facilitates communication with server 12 for installation on field devices, destination devices, or other devices, such as those associated with servers or systems 18, 20, 22 and 24. The regional network may then use server 12 to route event data and other patient data according to the user-configurable information.

Figure 9:
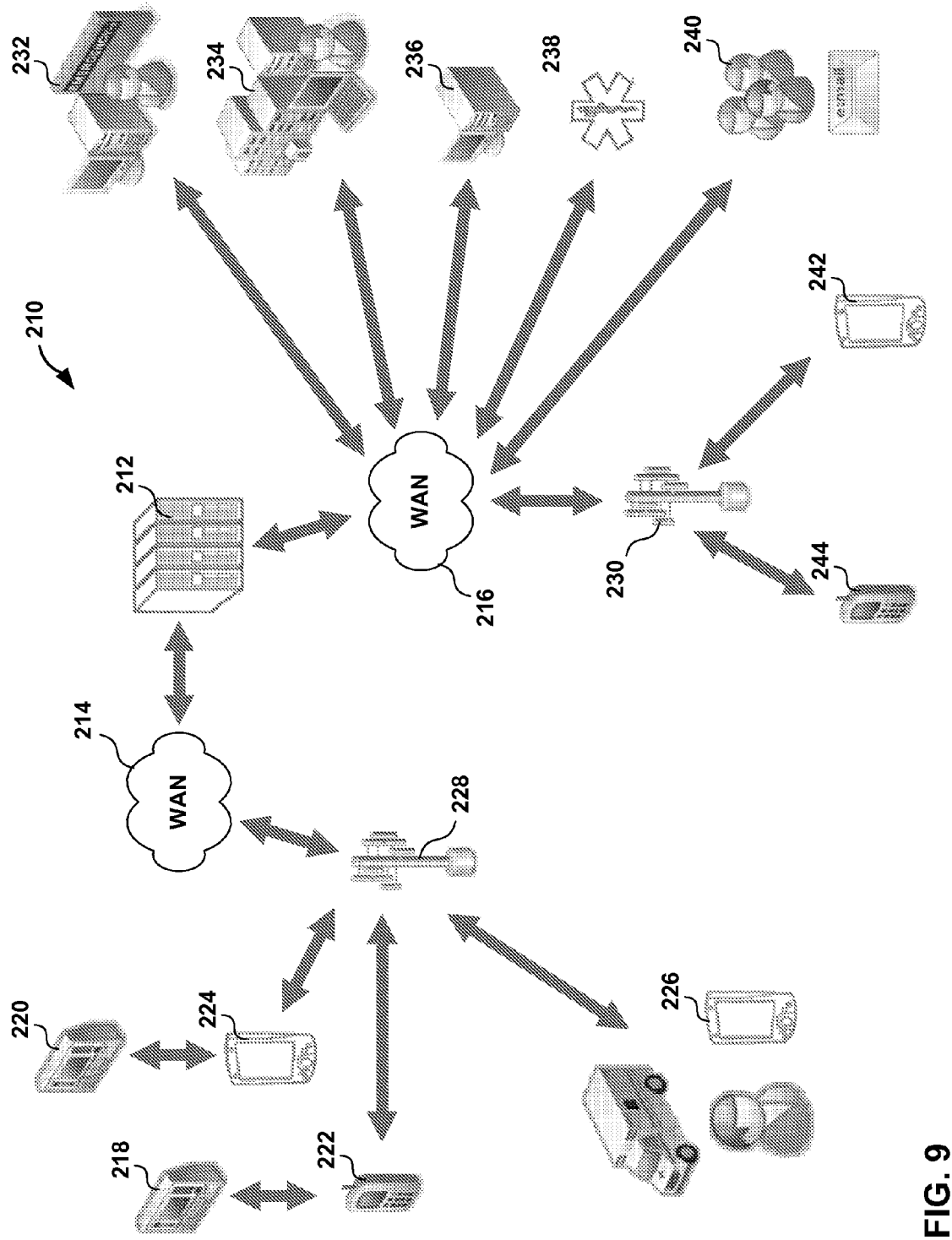
FIG. 9 is a conceptual diagram illustrating an example data transport system for routing medical event data in accordance with the techniques of this disclosure.

FIG. 9 is a schematic diagram of another example centralized data transfer system 210 designed in accordance with the techniques of this disclosure. Centralized data transfer system 210 includes central server 212, wide area networks (WANs) 214, 216, field devices 218, 220, gateways 222, 224, combined field device/gateway 226, cell towers 228, 230, and destinations 232, 234, 236, 238, 240, 242, 244. It should be noted that centralized data transfer system 210 illustrated in FIG. 9 is just one example of a centralized data transfer system and other embodiments may have more or less field devices and destinations in varying configurations. Although two WANs 214, 216 are illustrated, in other examples such WANs may be the same network, such as the Internet.

Field devices 218 and 220 transmit event data to gateways 222 and 224, respectively. Gateways 222, 224 then transmit the event data to cell tower 228, which in turn transmits the event data over wide area network 214. Central server 212 receives the event data over wide area network 214 and determines which destinations should receive the event data as well as how the event data should be formatted for each destination based on the routing and formatting techniques described in this disclosure. In some embodiments the routing and formatting determinations made by central server 212 may be based on user-configured rules and parameters. Central server 212 then routes formatted event data to the appropriate destinations 232, 234, 236, 238, 240, 242, 244 over wide area network 216. As shown in FIG. 9, a destination cell tower 230 may receive the formatted data from internet 216 and transmit the formatted data to other destinations 242, 244.

Field devices 218, 220 are provided for monitoring patient physiological symptoms and collecting patient and event data. Each field device may include any of a number of physiological monitoring devices and data collection devices. Field devices may also provide patient therapy. Field devices 218, 220 are shown in FIG. 9 as defibrillator/monitors. It should be noted, however, that the field devices need not be identical and may include a variety of different devices. Example field devices include an external defibrillator, a combined defibrillator/monitor, a standalone monitor, a 12-lead electrocardiograph, a perfusion sensor, a carbon-dioxide (CO2) sensor, a thermometer, or the like. Field devices 218, 220 may transmit the event data to internet gateways 222, 224 using a wireless personal area network (PAN) such as a network designed in accordance with the Bluetooth® specification, or by means of a cabled connection.

Gateways 222, 224 transmit event data to cell phone tower 228, which in turn transmits the event data over wide area network 214 to central server 212. A variety of gateway types and transmission links may be used within a single data transport system 210. For example, as shown in FIG. 9, gateway 222 is a cellular phone and gateway 224 is a tablet personal computer (PC). However, other combinations of gateways may be used within centralized data transfer system 210.

In some embodiments, the gateway transmits the event data to central server 212 over a Mobile Internet Protocol (IP) network, which may utilize a cellular telephone network infrastructure. For example, a gateway may include a cellular telephone, a personal digital assistant (PDA), or a tablet personal computer (PC) that is attached to a field device or carried by the EMS personnel who uses the field device. The gateway may receive event data from the field device, and software installed onto the gateway may transmit the event data over a secure internet protocol to the central server. In some embodiments, field devices 218, 220 may directly transmit data to server 212 via such a network and utilizing such a protocol, i.e., without the need for a mobile gateway.

In addition, some embodiments may have a combined field device/gateway, such as combined field device/gateway 226 illustrated in FIG. 9. Combined field device/gateway 226 may be a personal digital assistant (PDA), a tablet (PC) or some other non-therapeutic, non-monitoring data collection device and, in any case, may receive user input from emergency medical service (EMS) personnel. For example, EMS personnel may enter data such as a diagnosis or description of a patient's condition via a user interface on a PDA, a tablet PC, a defibrillator/monitor or other data collection device. In addition, the EMS personnel may enter patient demographic information, such as the patient's name, medical history, insurance information, or other identifying information. In addition, field devices 14 may be integrated with Electronic Patient Care Reporting (ePCR) products to collect and transmit patient demographic information. In this manner, a field device may collect and transmit patient physiological data as well as other patient and event data to central server 212.

Central server 212 receives the event data over wide area network 214 and determines which destinations should receive the event data as well as how the event data should be formatted for each destination based on the routing and formatting techniques described in this disclosure. In some embodiments the routing and formatting determinations made by central server 212 may be based on user-configured rules, information and parameters, as described above with respect to server 12 and system 10. Central server 212 then routes formatted event data to the appropriate destinations 232, 234, 236, 238, 240, 242, 244 over wide area network 216.

Destinations 232, 234, 236, 238, 240, 242, 244 are provided for receiving formatted event data from central server 212. When the event data is received at a destination, the destination may print a report, generate an audible notification, send an e-mail notification to a user, analyze the data, receive comments, forward the data and comments to another destination, or enable a user to view or print reports. The destinations may include specific devices associated with the one or more patient treatment centers, such as computing devices, displays, printers, cellular telephones, PDAs, or tablet PCs. Furthermore, destinations may include web-accessible accounts, such as an email account, which may allow a user to retrieve event data routed to a destination at a later, more convenient time.

Destinations may be associated with individual persons or with treatment centers. A destination associated with an individual person, such as a cardiologist or other physician, may include a cellular telephone, PDA, or tablet PC used by that cardiologist or physician. A destination associated with a treatment center may include a printer or receiving station. Destinations may also be classified as physical or logical. A physical destination refers to a device that has some sort of hardware or physical medium associated with the device, such as a printer, receiving station, cellular phone, or the like. A logical destination refers to an account or virtual device that does not have hardware or a physical medium associated with the device, such as an email or other web-accessible account, for example.

As one example, FIG. 9 illustrates an emergency department destination 232, which may be a referring hospital; a treatment center destination 234, which may be a treatment center having a catheterization laboratory; a receiving station 236 to receive and print reports as well as notifications; a regional registry 238; individual user e-mail accounts 240, a tablet PC 242, and a cell phone 244. Tablet PC 242 and cell phone 244 may receive event data and notifications by from cell tower 230, which in turn receives the data and notifications from central server 212 over wide area network 216. In some embodiments, wide area networks 216 and 218 may be the same network.

Various embodiments of the invention have been described. However, one of ordinary skill in the art will appreciate that various modifications may be made to the described system without departing from the scope of the claimed invention. For example, although described herein in the context of selective routing of ECGs from the field to various destinations at treatment centers, such as a catheterization lab, the invention is broadly applicable to the selective routing of any type of physiological data to any destination, which may improve the timeliness of any type of medical intervention. For example, user-configurable event data filtering rules may be used to selectively route data to appropriate destinations when the event data indicates stroke, diabetic shock, a particular type of trauma, hypothermia, contact with a poison or infectious disease, or an asthmatic attack.

Furthermore, the invention is not limited to the examples above. The above and other embodiments are within the scope of the following claims.

The invention claimed is:

1. A method comprising:
   receiving, at a server, event data for a patient from a field device used to at least one of monitor or treat the patient during an event, the server storing a plurality of destination profiles associated with respective destinations, the destinations associated with patient treatment centers, at least some of the destination profiles including respective event data filtering rules;
   analyzing the event data;
   applying the event data filtering rules by processing the analyzed event data from the server against the plurality of destination profiles associated with the respective destinations associated with the patient treatment centers;
   selecting a subset of the destinations based on the event data filtering rules;
   routing the event data from the server to the selected subset of the destinations; and
   determining a destination for the patient treatment center based on a match between the event data and the destination profiles.

2. The method of claim 1, further comprising:
   receiving configuration information from a user at the server; and
   configuring one of the event data filtering rules according to the configuration information.

3. The method of claim 1, wherein a first one of the destination profiles associated with a first one of the destinations of the subset further includes formatting information, the method further comprising formatting the event data routed to the first destination according to the formatting information.

4. The method of claim 3, further comprising:
   receiving configuration information from a user at the server; and
   configuring the formatting information for the first destination according to the configuration information.

5. The method of claim 1,
   wherein the server stores assignment information for the field device from which the event data was received, the assignment information associating the field device with a subset of the plurality of destinations,
   the method further comprising identifying as an initial subset of the destinations the subset of the destinations associated with the field device from which the event data was received based on the assignment information for the field device,
   wherein the selected subset of destinations is a subset of the initial subset of destinations.

6. The method of claim 1, further comprising:
   applying, with the server, one or more location rules to destination location information for at least some the destinations; and
   selecting an initial subset of the destinations based on the application of the one or more location rules to the destination location information,
   wherein the selected subset of destinations is a subset of the initial subset of destinations.

7. The method of claim 6,
   wherein the one or more location rules includes a rule that selects a treatment center based on at least one of proximity or travel time from the field device to the treatment center, and
   wherein the initial subset of destinations comprises destinations associated with the selected treatment center.

8. The method of claim 7, wherein the one or more location rules further includes a rule that selects a treatment center having a catheterization laboratory.

9. The method of claim 6,
   wherein the one or more location rules includes a rule that selects a physician based on at least one of proximity or travel time to a treatment center, and
   wherein the initial subset of destinations comprises a destination associated with the selected physician.

10. The method of claim 6, wherein the one or more location rules use an input received from a traffic condition source.

11. The method of claim 1, further comprising:
    retrieving scheduling information for at least some of the destinations;
    determining whether each of the at least some of the destinations is available based on the scheduling information for the destination;
    routing the event data to the destination if the destination is available; and
    not routing the event data to the destination if the destination is not available.

12. The method of claim 11,
    wherein the destination is associated with a physician, and
    wherein the scheduling information indicates whether the physician is on duty or on call.

13. The method of claim 1, wherein selecting the subset of the destinations comprises:
    analyzing the event data at the server; and
    selecting the subset of the destinations according to the analyzed data.

14. The method of claim 13, wherein routing the event data from the server to the selected subset of the destinations comprises, for each of the destinations with an associated event data filtering rule:
applying the event data filtering rule for the destination to the analyzed event data;
determining whether the event data filtering rule for the destination is satisfied;
routing the event data to the destination if the event data filtering rule is satisfied; and not
routing the event data to the destination device if the event data filtering rule is not satisfied.

15. The method of claim 14,
wherein the event data filtering rule for each of the destinations specifies at least one type of physiological data received by the destination,
wherein analyzing the event data comprises determining a data type for the physiological data, and
wherein determining whether the event data filtering rule for the destination is satisfied comprises comparing the data type for the physiological data to at least one type specified by the event data filtering rule.

16. The method of claim 14,
wherein, for at least some of the destinations, the event data filtering rule specifies that the destination receives one of all event data, event data with a 12-lead electrocardiogram (ECG), or event data that indicates that the patient is suspected of having suffered an acute myocardial infarction (AMI),
wherein analyzing the event data and determining whether the event data filtering rule for the destination is satisfied comprises:
determining whether the event data comprises a 12-lead ECG data; and
determining from the event data whether the patient is suspected of having suffered an acute myocardial infarction (AMI).

17. The method of claim 16, wherein determining from the event data whether the patient is suspected of having suffered an AMI comprises analyzing an ECG of the patient by the server.

18. The method of claim 17, wherein analyzing an ECG of the patient comprises:
retrieving one or more past ECGs of the patient from a patient medical record database with the server; and
comparing the ECG of the patient to the one or more past ECGs.

19. The method of claim 1, wherein the event data further includes information entered into the field device by emergency medical service (EMS) personnel.

20. The method of claim 1, further comprising:
retrieving data of the patient from a patient medical record database with the server; and routing the retrieved data with the event data.

21. The method of claim 1, wherein the event data includes patient demographic data.

22. The method of claim 1, wherein the field device comprises an external defibrillator.

23. The method of claim 1, wherein the destinations comprise at least one of computing devices, displays, printers, cellular telephones, personal digital assistants, or web-accessible accounts.

24. The method of claim 1, wherein receiving event data comprises receiving the event data via a Mobile Internet Protocol network.

25. The method of claim 1, further comprising, with the server:
collecting a first time for an event from a first device;
collecting a second time for the event from a second device; and
calculating a treatment time interval for the event based on the first and second times.

26. The method of claim 25, further comprising storing the treatment time interval in the server for use in future event data routing decisions.

27. The method of claim 25, wherein collecting a second time comprises collecting a time of a percutaneous transluminal coronary intervention.

28. The method of claim 1, wherein the event data is selected from the group comprising patient physiological data, patient condition medical data, electrocardiogram data, capnography data, carbon dioxide data, emergency medical service personnel input data, medical device data, global positioning systems data.

29. A network server comprising:
a memory that stores a plurality of destination profiles, each of the destination profiles associated with a respective one of a plurality of destinations that are associated with a network of patient treatment centers, wherein at least some of the destination profiles include at least one event data filtering rule for the respective destination; and
a processor that:
receives event data for a patient from a field device used to at least one of monitor or treat the patient during an event;
analyzes the event data;
applies at least one of the data filtering rules by processing the analyzed event data from the server against the plurality of destination profiles associated with the respective destinations associated with the patient treatment centers;
selects a subset of the destinations based on applying the content of the event data to the event data filtering rules;
routes the event data from the server to the selected subset of the destinations; and
determines a destination for the patient treatment center based on a match between the event data and the destination profiles.

30. The network server of claim 29, wherein the processor receives configuration information from a user, and configures the event data filtering rule of one or more of the plurality of destination profiles according to the configuration information.

31. The server of claim 29,
wherein the processor applies one or more location rules to destination location information for at least some of the destinations, and selects an initial subset of the destinations based on the application of the one or more location rules to the destination location information, and
wherein the selected subset of destinations is a subset of the initial subset of destinations.

32. The server of claim 31,
wherein the one or more location rules includes a rule that selects a treatment center based on at least one of proximity or travel time from the field device to the treatment center, and
wherein the initial subset of destinations comprises destinations associated with the selected treatment center.

33. The server of claim 31,
wherein the one or more location rules includes a rule that selects a physician based on at least one of proximity or travel time to a treatment center, and wherein the initial subset of destinations comprises a destination associated with the selected physician.

34. The server of claim 31, wherein the one or more location rules use an input received from a traffic condition source.

35. The server of claim 29, wherein the processor:
retrieves scheduling information for at least some of the destinations;
determines whether each of the at least some of the destinations is available based on the scheduling information for the destination;
routes the event data to the destination if the destination is available; and
does not route the event data to the destination if the destination is not available.

36. The server of claim 29, wherein the processor analyzes the event data, and selects the subset of the destinations according to the analyzed event data.

37. The server of claim 36, wherein, for each of the destinations with an associated event data filtering rule, the processor:
applies the event data filtering rule for the destination to the analyzed event data; determines whether the event data filtering rule for the destination is satisfied; routes the event data to the destination if the event data filtering rule is satisfied; and
does not route the event data to the destination device if the event data filtering rule is not satisfied.

38. The server of claim 37,
wherein the event data filtering rule for each of the destinations specifies at least one type of physiological data received by the destination, and
wherein the processor identifies a data type for the physiological data, and compares the data type for the physiological data to at least one type specified by the event data filtering rule to determine whether the rule is satisfied.

39. The server of claim 37,
wherein, for at least some of the destinations, the event data filtering rule specifies that the destination receives one of all event data, event data with a 12-lead electrocardiogram (ECG), or event data that indicates that the patient is suspected of having suffered an acute myocardial infarction (AMI), and
wherein the processor determines whether the event data comprises a 12-lead ECG data and determines from the event data whether the patient is suspected of having suffered an acute myocardial infarction (AMI) in order to determine whether the rules for the various destinations are satisfied.

40. The server of claim 39, wherein the processor analyzes an ECG of the patient to determine from the event data whether the patient is suspected of having suffered an AMI.

41. The server of claim 29, wherein the processor:
collects a first time for an event from a first device;
collects a second time for the event from a second device; and
calculates a treatment time interval for the event based on the first and second times.

42. The server of claim 41, wherein the second time comprises a time of a percutaneous transluminal coronary intervention.

43. A non-transitory computer-readable medium comprising instructions that cause a programmable processor of a network server to:
receive event data for a patient from a field device used to at least one of monitor or treat the patient during an event, the server storing a plurality of destination profiles associated with respective destinations, the destinations associated with patient treatment centers, at least some of the destination profiles including respective event data filtering rules;
analyze the event data;
apply at least one of the data filtering rules by processing the analyzed event data from the server against the plurality of destination profiles associated with the respective destinations associated with the patient treatment centers;
select a subset of the destinations based on the event data filtering rules;
route the event data from the server to the selected subset of the destinations; and
determine a destination for the patient treatment center based on a match between the event data and the destination profiles.

44. A system for managing communication of patient data within a regional patient treatment network that includes at least one emergency medical service and a plurality of patient treatment centers, the system comprising:
a plurality of field devices associated with the emergency medical service;
a plurality of destinations, each of the destinations associated with at least one of the patient treatment centers; and
a network server that:
stores a plurality of destination profiles, each of the destination profiles associated with a respective one of the plurality of destinations, wherein at least some of the destination profiles includes at least one event data filtering rule for the respective destination;
receives event data for a patient from one of the field devices used to at least one of monitor or treat the patient during an event;
analyzes the event data;
applies at least one of the data filtering rules by processing the analyzed event data from the server against the plurality of destination profiles associated with the respective destinations associated with the patient treatment centers;
selects a subset of the destinations based on applying the event data to the event data filtering rules;
routes the event data to the selected subset of the destinations; and
determines a destination for the patient treatment center based on a match between the event data and the destination profiles.

45. The system of claim 44, wherein the server:
stores assignment information for at least the field device from which the event data was received, the assignment information associating the field device with a respective subset of the plurality to destinations; and
identifies as an initial subset of the destinations the respective subset of the destinations associated with the field device from which the event data was received by the assignment information for the field device,
wherein the selected subset of destinations is a subset of the initial subset of destinations.

46. The system of claim 44, wherein the server:
applies one or more location rules to destination location information for at least some of the destinations; and
selects an initial subset of the destinations based on the application of the one or more location rules to the destination location information, wherein the selected subset of destinations is a subset of the initial subset of destinations.

47. The system of claim 46,
wherein the one or more location rules includes a rule that selects one of the treatment centers based on at least one of proximity or travel time from the field device to the treatment center, and
wherein the initial subset of destinations comprises destinations associated with the selected treatment center.

48. The system of claim 47, wherein the one or more location rules further includes a rule that selects one of the treatment centers having a catheterization laboratory.

49. The system of claim 44, wherein the field device comprise external defibrillators.

50. The system of claim 43, wherein the destinations comprise at least one of computing devices, displays, printers, cellular telephones, personal digital assistants, or web-accessible accounts associated with at least one of treatment centers or a physician associated with at least one of the treatment centers.

51. The system of claim 44, wherein the field devices and the server communicate via a Mobile Internet Protocol network.

* * * * *

UNITED STATES PATENT AND TRADEMARK OFFICE
CERTIFICATE OF CORRECTION

| | |
|---|---|
| PATENT NO. | : 8,185,623 B2 |
| APPLICATION NO. | : 12/394881 |
| DATED | : May 22, 2012 |
| INVENTOR(S) | : Dana Lewis, Randy L. Merry and Richard C. Nova |

It is certified that error appears in the above-identified patent and that said Letters Patent is hereby corrected as shown below:

In Column 28, line 3, Claim 50 should read "The system of claim 44, wherein the destinations com-"

Signed and Sealed this
Twenty-fifth Day of September, 2012

David J. Kappos
*Director of the United States Patent and Trademark Office*